(12) United States Patent
Nordquist et al.

(10) Patent No.: US 6,479,704 B1
(45) Date of Patent: Nov. 12, 2002

(54) HYDROGENATION WITH MONOLITH REACTOR UNDER CONDITIONS OF IMMISCIBLE LIQUID PHASES

(75) Inventors: Andrew Francis Nordquist, Whitehall; Frederick Carl Wilhelm, Zionsville; Francis Joseph Waller; Reinaldo Mario Machado, both of Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/839,699

(22) Filed: Apr. 20, 2001

(51) Int. Cl.$^7$ .............................................. C07C 209/00
(52) U.S. Cl. ...................... 564/423; 564/397; 564/398; 564/417; 564/420; 564/422; 549/308; 549/325; 549/508
(58) Field of Search ................................ 564/397, 398, 564/417, 423, 420, 422; 549/308, 325, 508

(56) References Cited

U.S. PATENT DOCUMENTS

| | | | |
|---|---|---|---|
| 4,743,577 A | 5/1988 | Schroeder et al. | 502/326 |
| 5,250,490 A | 10/1993 | Ritscher et al. | 502/313 |
| 6,005,143 A | 12/1999 | Machado et al. | 564/423 |

FOREIGN PATENT DOCUMENTS

EP 0233642 8/1987

OTHER PUBLICATIONS

Hatziantoniou, et al. "The Segmented Two–Phase Flow Monolithic Catalyst Reactor. An Alternative for Liquid–Phase Hydrogenations", Ind. Eng. Chem. Fundam., Vo. 23, No. 1, 82–88 (1984).
Hatziantoniu, et al. "Mass Transfer and Selectivity in Liquid–Phase Hydrogenation of Nitro Compounds in a Monolithic Catalyst Reactor with Segmented Gas–Liquid Flow", Ind. Eng. Chem. Process Des. Dev., vol. No. 4, 964–970 (1986).
Report by Delf University, Elsevier Science B.V., Preparation of Catlaysts VII, pp 175–483 (1998).

*Primary Examiner*—Samuel Barts
(74) *Attorney, Agent, or Firm*—Keith D. Gourley

(57) ABSTRACT

The present invention relates to an improved for the hydrogenation of an immiscible mixture of an organic reactant in water. The immiscible mixture can result from the generation of water by the hydrogenation reaction itself or, by the addition of, water to the reactant prior to contact with the catalyst. The improvement resides in effecting the hydrogenation reaction in a monolith catalytic reactor from 100 to 800 cpi, at a superficial velocity of from 0.1 to 2 m/second in the absence of a cosolvent for the immiscible mixture. In a preferred embodiment, the hydrogenation is carried out using a monolith support which has a polymer network/carbon coating onto which a transition metal is deposited.

16 Claims, No Drawings

HYDROGENATION WITH MONOLITH REACTOR UNDER CONDITIONS OF IMMISCIBLE LIQUID PHASES

GOVERNMENT CONTRACT

This invention was made under Government Contract No DE-FC02-CH11018 with the U.S. Department of Energy.

BACKGROUND OF THE INVENTION

Industrial hydrogenation reactions are often performed by using finely divided powdered slurry catalysts in stirred-tank reactors. These slurry phase reaction systems are inherently problematic in chemical process safety, operability and productivity. The finely divided, powdered catalysts are often pyrophoric and require extensive operator handling during reactor charging and filtration. By the nature of their heat cycles for start-up and shut-down, slurry systems promote co-product formation which can shorten catalyst life and lower yield to the desired product.

An option to the use of finely divided powder catalysts in stirred reactors has been the use of pelleted catalysts in fixed bed reactors. While this reactor technology does eliminate much of the handling and waste problems, a number of engineering challenges have not permitted the application of fixed bed reactor technology to the hydrogenation of many organic compounds. Controlling the overall temperature rise and temperature gradients in the reaction process has been one problem. A second problem is that in fixed bed packed reactors there is a significant pressure drop due to the high flow rates required for hydrogenation. A third problem is that liquid-gas distribution is problematic thus often leading to poor conversion and localized concentration gradients. A fourth problem is that the product water phase in a two liquid phase system tends to block access of the reactant to the active catalyst sites and thereby decrease the reaction rate or, in the alternative result, inconsistent reaction rates.

Monolith catalysts are an alternative to fixed bed reactors and have a number of advantages over conventional fixed bed reactors. These reactors have low pressure drop which allow them to be operated at higher gas and liquid velocities. These higher velocities of gas and liquids promote high mass transfer and mixing and the parallel channel design of a monolith inhibits the coalesence of the gas in the liquid phase.

The following articles and patents are representative of catalytic processes employing monolith catalysts and processes in chemical reactions including the hydrogenation of nitroaromatics and other organic compounds.

Hatziantoniou, et al. in "The Segmented Two-Phase Flow Monolithic Catalyst Reactor. An Alternative for Liquid-Phase Hydrogenations", Ind. Eng. Chem. Fundam., Vol. 23, No.1, 82–88 (1984) discloses the liquid phase hydrogenation of nitrobenzoic acid (NBA) to aminobenzoic acid (ABA) in the presence of a solid palladium monolithic catalyst. The monolithic catalyst consisted of a number of parallel plates separated from each other by corrugated planes forming a system of parallel channels having a cross sectional area of 1 mm$^2$ per channel. The composition of the monolith comprised a mixture of glass, silica, alumina, and minor amounts of other oxides reinforced by asbestos fibers with palladium metal incorporated into the monolith in an amount of 2.5% palladium by weight. The reactor system was operated as a simulated, isothermal batch process. Feed concentrations between 50 and 100 moles /m$^3$ were cycled through the reactor with less than 10% conversion per pass until the final conversion was between 50% and 98%.

Hatziantoniou, et al. in "Mass Transfer and Selectivity in Liquid-Phase Hydrogenation of Nitro Compounds in a Monolithic Catalyst Reactor with Segmented Gas-Liquid Flow", Ind. Eng. Chem. Process Des. Dev., Vol. 25, No.4, 964–970 (1986) discloses the isothermal hydrogenation of nitrobenzene and m-nitrotoluene dissolved in ethanol using a monolithic catalyst impregnated with palladium. The authors report that the activity of the catalyst is high and therefore mass-transfer is rate determining. Hydrogenation was carried out at 590 and 980 kPa at temperatures of 73 and 103° C. Again, less than 10% conversion per pass was achieved. Ethanol was used as a co-solvent to maintain one homogeneous phase.

U.S. Pat. No. 6,005,143 discloses a process for the adiabatic hydrogenation of dinitrotoluene in a monolith catalyst employing nickel and palladium as the catalytic metals. A single phase dinitrotoluene/water mixture in the absence of solvent is cycled through the monolith catalyst under plug flow conditions for producing toluenediamine.

U.S. Pat. No. 4,743,577 discloses metallic catalysts which are extended as thin surface layers upon a porous, sintered metal substrate for use in hydrogenation and decarbonylation reactions. In forming a monolith, a first active catalytic material, such as palladium, is extended as a thin metallic layer upon a surface of a second metal present in the form of porous, sintered substrate. The resulting catalyst is used for hydrogenation, deoxygenation and other chemical reactions. The monolithic metal catalyst incorporates catalytic materials, such as, palladium, nickel and rhodium, as well as platinum, copper, ruthenium, cobalt and mixtures. Support metals include titanium, zirconium, tungsten, chromium, nickel and alloys.

U.S. Pat. No. 5,250,490 discloses a catalyst made by an electrolysis process for use in a variety of chemical reactions such as hydrogenation, deamination, amination and so forth. The catalyst is comprised of a noble metal deposited, or fixed in place, on a base metal, the base metal being in form of sheets, wire gauze, spiral windings and so forth. The preferred base metal is steel which has a low surface area, e.g., less than 1 square meter per gram of material. Catalytic metals which can be used to form the catalysts include platinum, rhodium, ruthenium, palladium, iridium and the like.

EPO 0 233 642 discloses a process for hydrogenation of organic compounds in the presence of a monolith-supported hydrogenation catalyst. A catalytic metal, e.g., Pd, Pt, Ni, or Cu is deposited or impregnated on or in the monolith support. A variety of organic compounds are suggested as being suited for use and these include olefins, nitroaromatics and fatty oils.

There is a report by Delft University, in Elsevier Science B.V., Preparation of Catalysts VII, p. 175–183 (1998) that discloses carbon coated ceramic monoliths where the carbon serves as a support for catalytic metals. Ceramic monoliths were dipped in furfuryl alcohol based polymers and the polymers allowed to polymerize. After solidification the polymers were carbonized in flowing argon to temperatures of 550° C. followed by partial oxidation in 10% $O_2$ in argon at 350° C. The carbon coated monolith typically had a surface area of 40–70 m$^2$/gram.

BRIEF SUMMARY OF THE INVENTION

The present invention relates to an improved process for the hydrogenation of an immiscible mixture of an organic reactant in water. The two phase immiscible mixture can result from the generation of water during the hydrogenation reaction itself or, by the addition of water to the reactant prior to contact with the catalyst. The improvement resides in effecting the hydrogenation of a two phase immiscible mixture of organic reactant in water in a monolith catalytic reactor having from 100 to 800 cells per square inch (cpi), and passing the two phase immiscible mixture of organic reactant in water through the reactor at a superficial velocity of from 0.1 to 2 m/second in the absence of a cosolvent for the two phase immiscible mixture. In a preferred embodiment, the hydrogenation is carried out using a monolith support with a polymer network/carbon coating and a transition metal catalyst.

Several advantages are achievable in the process through the use of a monolith support and these include:

an ability to effect liquid phase hydrogenation of organic compounds as an immiscible phase in water and in the absence of a cosolvent;

an ability to obtain high throughput of product through the catalytic unit even though the reaction rate may be less than that using a cosolvent;

an ability to effect hydrogenation reactions at a consistent reaction rate; and, an ability to hydrogenate organic reactants under liquid phase conditions that permit ease of separation of reactants and byproduct;

DETAILED DESCRIPTION OF THE INVENTION

The present invention relates to an improved process for the hydrogenation of an immiscible mixture (two phases) of an organic reactant in water. The immiscible mixture can result from the generation of water during the hydrogenation reaction or, if desired, by the addition of water to the reactant prior to contact with the catalyst.

There are numerous categories of organic compounds having functional groups that may be hydrogenated as a two phase mixture. The functional group containing compounds include nitro-organics, acid anhydrides and the reaction products of a ketone or aldehyde with ammonia or a primary or secondary amine. The following are hydrogenation reactions involving these functional groups that co-produce water and can be hydrogenated in a monolith reactor.

Nitro Group Reduction

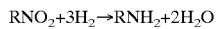
$RNO_2 + 3H_2 \rightarrow RNH_2 + 2H_2O$ where R is aromatic. Many nitro aromatics are capable of undergoing the hydrogenation reaction described by the process of this invention. Typical nitroaromatics are nitrobenzene, nitrotoluenes, nitroxylenes, nitroanisoles and halogenated nitroaromatics where the halogen is Cl, Br, I, or F.

Anhydride Reduction to Lactone or Ether

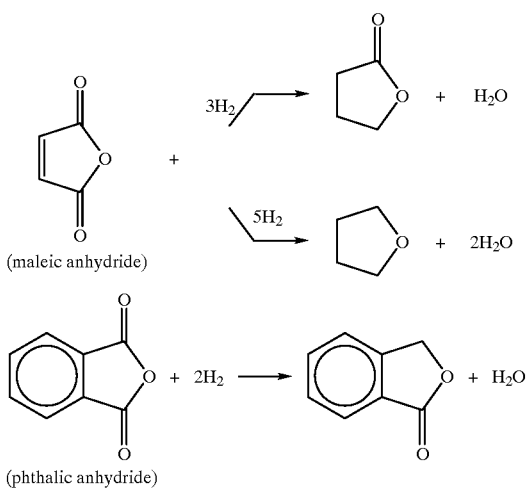

(maleic anhydride)

(phthalic anhydride)

Anhydrides such as maleic anhydride and phthalic anhydride are first hydrogenated to γ-butyrolactone and phthalide respectively. The γ-butyrolactone can be further reduced to tetrahydrofuran.

Reductive Alkylation or Reductive Amination

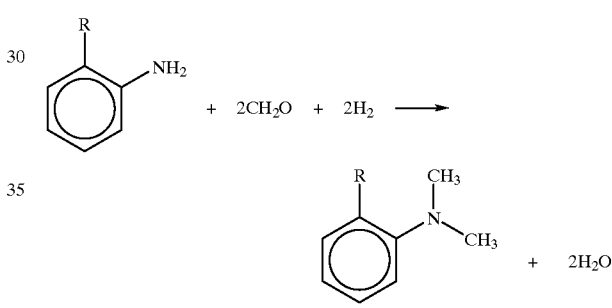

R'CHO + NH$_3$ + H$_2$ ⟶ R'CH$_2$NH$_2$ + H$_2$O

When an aldehyde or a ketone is treated with ammonia or a primary or secondary amine in the presence of hydrogen and a hydrogenation catalyst, reductive alkylation of ammonia or the amine or reductive amination of the carbonyl compound takes place. R and R' can be aromatic or aliphatic. Examples of aldehydes and ketones useful in the hydrogenation reactions include formaldehyde, cyclohexanone and methyl isopropyl ketone. Reaction products resulting from the reaction of these aldehydes and ketones with primary and secondary amines include N-methylcyclohexylamine, N-methyldicyclohexylamine, N,N-dimethylcyclohexylamine, N-ethylcyclohexylamine, dicyclohexylamine, N,N-diethylcyclohexylamine, N, N, N'-trimethylaminoethylethanolamine, N-ethyl-1,2-dimethylpropylamine and N,N,N',N'-tetramethylpropanediamine.

By immiscibility of the reaction system leading to the presence of two phases, it is meant that two liquid phases are present at the operating temperature. The solubility of the organic reactant in water is not only a function of temperature but also a function of the solubility of the reaction product(s) with the organic reactant and with water. In some hydrogenation reaction systems, e.g., the hydrogenation of dinitrotoluene, the dinitrotoluene reactant, the toluenediamine reaction product and water produce essentially one liquid phase at stoichiometric reaction conditions of 60% toluenediamine, 39% water and 1% dinitrotoluene. In the hydrogenation of nitrobenzene, however, the reaction products of nitrobenzene, aniline and water, on the other hand, remain as a two phase system throughout the hydrogenation process. The following solubility data is for aniline in water and nitrobenzene in water at different temperatures.

|  | Temperature | | |
| --- | --- | --- | --- |
|  | 20° C. | 80° C. | 90° C. |
| aniline | 3.4 g per 100 g $H_2O$ | — | 6.4 g per 100 g $H_2O$ |
| nitrobenzene | 0.19 g per 100 g $H_2O$ | 0.8 g per 100 g $H_2O$ | — |

Monolith catalysts employed in the process described herein consist of an inorganic porous substrate, a metallic substrate, or a modified substrate coated with a catalytic metal. The modification can be a coating derived from a carbon or a heat treated network polymer. Often the monoliths are based upon a honeycomb of long narrow capillary channels, circular, square, rectangular or other geometric shape, whereby gas and liquid are co-currently passed through the channels under a laminar flow regime. The flow of gas and liquid in these confined channels and under these conditions promotes "Taylor" flow with bubbles of $H_2$ gas squeezing past the liquid. This capillary action promotes very high initial gas-liquid and liquid-solid mass transfer.

The pressure drop within an effective monolith reactor can range from 2 kPa/m to 200 kPa/m for combined gas/liquid superficial velocities between 0.1 to 2 meters/second for 50% gas holdup in a monolith reactor having 400 cpi (cells per square inch). Typical dimensions for a honeycomb monolith cell wall spacings range from 1 to 10 mm between the plates. Alternatively, the monolith may have from 100 to 800, preferably 200 to 600 cpi. Channels may be square, hexagonal, circular, elliptical, etc. in shape.

Catalytic metals suited for the hydrogenation of water immiscible organics are impregnated or directly coated onto the monolithic substrate, a modified substrate or a washcoat which has been deposited onto the monolith. The catalytic metals include those Group VIb, Group VIIb, Group VIII, and Group Ib metals of the periodic table and conventionally used in hydrogenation reactions. Examples of catalytic metal components include cobalt, Raney or sponge nickel, palladium, platinum, copper, ruthenium, rhenium and so forth. Often a mixture of metals are employed, one example being palladium and nickel. For a monolith catalyst impregnated with a washcoat the composition of catalytic metals is typically identified as a weight percent within the washcoat itself. The washcoat may be applied in an amount of from 1 to 50% of the monolith total weight. Typical catalyst metal loadings, then, range from 0.1 to 25% by weight and preferably from 1 to 10% by weight of the washcoat. The catalytic metals may be incorporated into the monolith in a manner generally recognized by the art. Incipient wetness from a salt solution of the catalytic metal is one example of a method for incorporating a metal catalytic component on the monolith substrate or modified monolith.

The superficial liquid and gas velocities in the monolith channels are maintained to effect a desired conversion, e.g., 1% to 99% per pass. Typically, the superficial velocity through the monolith ranges between 0.1 to 2 meters per second with residence times of from 0.5 to 120 seconds.

Although not intending to be bound by theory, when a monolith is used as a catalyst support, the morphology of the monolith surface is important in order to (a) attach the active metal for hydrogenation and (b) in the case of two immiscible liquid phases selectively adsorb the reactant over the other immiscible phase, water, and the product.

In terms of a catalyst support, particularly a carbon film acting as a support for the metal, eliminating microporosity of the carbon surface is advantageous for fast reaction rates and long catalyst life. Small and medium size pores in the surface tend to lead to catalyst deactivation through pore plugging with high molecular weight co-products. Therefore, the carbon monolith, a carbon coated monolith or a polymer network/carbon coated monolith should have a very low surface area for optimum activity, i.e., a $N_2$ BET of from approximately 1 to 15 $m^2$/gram of total surface area of monolith catalyst.

To achieve a polymer network/carbon coated monolith having low surface area, polymer coating solutions may be applied to the wall surface and heated below traditional carbonization temperatures. Examples of polymer solutions include furfuryl alcohol and furfuryl alcohol with other additives such as pyrrole and polyethylene glycol methyl ether; epoxy resins with amines; epoxy resins with anhydrides; saturated polyester with glycerol or other multifunctional alcohols; oil-modified alkyd saturated polyesters, unsaturated polyesters; polyamides; polyimides; phenol/formaldehyde; urea/formaldehyde; melamine/formaldehyde and others. The above procedure can be modified by using a commercially available oligomer or copolymer of furfuryl alcohol.

Carbonization of the polymer coating is effected at relatively low temperature. Temperatures for carbonization range from 250 to 350° C. vs 550–900° C. commonly used in the prior art. Because of the lower carbonization temperatures used herein, these networked polymers having polar groups will retain some of their functionality and are more like the polymer than carbon. These functional groups can be coupled through reaction chemistry to anchor homogeneous catalyst, homogeneous chiral catalysts or ligands to the polymeric surface. They also have significantly lower surface areas, as stated, supra.

The hydrogenation is effected at temperatures of 60–180° C. The hydrogenation pressure can be up to 1600 psig.

The following examples are intended to represent various embodiments of the invention and are not intended to restrict the scope thereof.

Preparation of Low Surface Area Polymer Network/Carbon Coated Monolith

General Procedure

Coating: A network polymer resin can be made from the polymerization of the appropriate monomers or oligomers. As an example furfuryl alcohol is polymerized with an acid at a controlled temperature to produce a coating solution. The acid can be inorganic (i.e. $HNO_3$, HCl, $H_2SO_4$) or organic (i.e. aromatic sulfonic). A dried monolith is then soaked in the coating solution for 2–4 minutes, allowed to drip dry (removal of excess coating solution from the channels) and let dry. The channels are blown clear with air if it is observed that the monolith channels have become visually blocked by the polymer solution. The coated monolith is further dried at 80° C. under a $N_2$ purge overnight.

Carbonization: The coated monolith is mounted in a tube furnace and purged with $N_2$ while the heat is increased to 110° C. for 30 minutes. The tube is then continued to be heated until the tube surface temperature is 280° C. and held at 280° C. for 2 hours. The furnace is cooled to 260° C. and 5% $O_2$/He is introduced instead of the $N_2$. The tube containing the monolith is heated to 280° C. and held there for 40 minutes. The carrier gas is switched back to $N_2$ and the heat is turned off. The monolith is removed after reaching room temperature.

Metal Impregnation: The catalytically active metal is incorporated onto the monolith by incipient wetness techniques, dried at 80° C. in an oven overnight with $N_2$ purge and then calcined at a tube surface temperature of 280° C. using $N_2$. The modified monolith is now ready to be used as a hydrogenation catalyst. The modified monolith could also be pre-reduced before being used as a catalyst. To be more specific, after the carbonization the amount of metal salt to dissolve or standard metal solution to dilute based on previously determined pore volume is calculated. In a typical example of metal impregnation, a 2" diameter 400 cpi cordierite monolith 2" in height is placed in a glass beaker containing approximately 80 ml of active metal solution. Additional solution is added to cover the monolith if necessary. The monolith is soaked for approximately 30 minutes or until no bubbles are seen. The solution is poured from the container, the monolith is removed and excess solution from channels is cleared by a low flow of air. The monolith is set in the hood for approximately 1 hr., and periodically checked to see if channels remain cleared. If channels are not clear, blow through with low flow of air. The monolith is placed in an 80° C. oven with $N_2$ purge overnight. After removal of the monolith from the oven, let it cool in a desiccator. The monolith is then heated in a tube furnace at a tube surface temperature of 280° C. using $N_2$ for 2 hours.

Hydrogenation Rate Determination in Monolith Screening Reactor

A 2-liter batch autoclave reactor was fitted with a dual-function impeller, oriented above a catalyst holder for the monolith, capable of inducing gas and pumping the gas-liquid dispersion through the catalyst bed. For the reactions studied, the typical combined liquid volume of reagents was 1 liter. The autoclave reactor was equipped with a dip tube to transfer the liquid reaction solution to a recovery cylinder. The portion of the reaction solution which was removed, was diluted and an internal standard added. Gas chromatography was used to perform a quantitative product analysis to calculate selectivity and conversion.

The raw hydrogen pressure data was corrected for compressibility. A hydrogen uptake curve was obtained as a function of reaction time. This curve was used to calculate rate data at various stages of conversion.

COMPARATIVE EXAMPLE 1

Hydrogenation of Nitrobenzene in Monolith Catalyst Using a Cosolvent, Isopropanol A series of monolith hydrogenation catalysts having varying organic coatings was used to effect the hydrogenation of nitrobenzene (NB). Hydrogenation was carried out at a concentration of 40 wt. % NB in isopropanol and the rate of hydrogenation was measured at 50% conversion. All of these monolithic hydrogenation catalysts were tested in one liquid phase. Isopropyl alcohol was added as a solvent in order to make miscible the two immiscible phases of nitrobenzene and water. Reaction conditions consisted of 120° C., 200 psig $H_2$ at a stirring rate of 1500 rpm.

The column in Table 1 marked initial rate is the second experimental run in the batch autoclave and the column marked final rate is the eighth experiment at the same set of conditions and using the same catalyst. The rate, at 50% conversion, is expressed in moles $H_2$ per $m^3$ catalyst per second. Selectively in mol % is determined at 100% conversion in the second experimental run. The $N_2$ BET method was used to measure total surface area of monolith catalyst and the units are in $m^2$/gram. All % Pd are wt. % and based on total monolith weight.

TABLE 1

Pd on Carbon Monolith Hydrogenation Catalyst in One Liquid Phase

| Catalyst | Layer | Comment | Rate[1] (initial) | Rate (final) | Sel. to Aniline | $N_2$ BET ($m^2$/gm) |
|---|---|---|---|---|---|---|
| A | polymer network/carbon | 1.5% Pd/C/cordierite[2] | 92 | 91 | 97 | <1 |
| B | polymer network/carbon | 3.1% Pd/C/cordierite[3] | 61 | 74 | 97 | 12 |
| C | polymer network/carbon | 2% Pd/C/cordierite[4,5] | 47 | 20 | 97 | <1 |
| D | carbon composite | 1.7% Pd on C[5] | 20 | 13 | 98 | 466 |
| E | carbon composite | 4.6% Pd on C[4,5] | 36 | 23 | 93 | 372 |
| F | polymer network/carbon | 2% Pd/C/cordierite[4,6] | 87 | 46 | 99 | <1 |
| G (control) | no carbon | 2% Pd/cordierite | 33 | 16 | 98 | <1 |

[1]Moles $H_2$ per $m^3$ catalyst per second
[2]Furfuryl alcohol network polymer coating, low temperature carbonization, metal deposition, calcination as in general procedure
[3]Same catalyst formulation as Catalyst A-Higher Pd loading-Carbonization temperature is 550° C.
[4]Metal deposition and calcination as in general procedure
[5]C, D and E are developmental monoliths from commercial vendors
[6]The coating was made from a phenolic resin (Varcum)

Table 1 shows a general inverse trend between initial hydrogenation rate and surface area of the polymer network/carbon layer independent of catalyst loading. Surfaces having a $N_2$ BET of 15 or less $m^2$/gram provided high initial and final hydrogenation reaction rates. This is contrary to the teachings in the scientific literature that a high surface area catalyst is more catalytically active. Except for one carbon monolith from a commercial vendor, all monolith catalysts, either carbon or polymer network/carbon, were more active than the control, Catalyst G, which did not have any carbon or added layer. In addition, the organic coatings made from furfuryl alcohol or a phenolic resin both have a low surface area layer and high initial hydrogenation rates. But, the furfuryl alcohol based layer, Catalysts A and B, did not show a drop in hydrogenation activity after 8 runs. Catalyst A which was carbonized at a low temperature and therefore retained some functionality vis-à-vis Catalyst B had significantly higher initial and final hydrogenation rates even at a lower catalyst metal loading. Except for Catalyst E (carbon composite monolith) all catalysts gave aniline selectivity greater than approximately 97 mol %.

EXAMPLE 2

Evaluation of Monolith Catalysts For Nitrobenzene Hydrogenation Without a Cosolvent-Two-Phase A series of polymer network/carbon coated cordierite hydrogenation catalysts were tested using neat nitrobenzene as the reactant. Conditions were similar to Example 1 except that the reaction system comprised two liquid phases. These results are shown in Table 2.

TABLE 2

Pd on Carbon Monolith Hydrogenation Catalyst in Two Immiscible Phases

| Catalyst | Layer | Rate[1] (initial) | Sel to Aniline |
|---|---|---|---|
| A | polymer network/carbon | 42 | 99 |
| B | polymer network/carbon | 44 | 99 |
| F | polymer network/carbon | 33 | 99 |

[1]moles $H_2$ per $m^3$ catalyst per second; 120° C.; 200 psig; 1500 rpm

In each run the hydrogen uptake curve when re-plotted as the hydrogenation rate vs time showed that the hydrogenation rate was nearly constant until toward the end of the reaction. The nearly constant hydrogenation rate was not expected since the co-product, water, is being formed during the reaction and two immiscible phases are present. As the concentration of the water increased it was expected that the hydrogenation rate should decrease, or become inconsistent. These results suggest that the hydrophobic surface layer may selectively adsorb the nitrobenzene to the catalytically active surface since these three monoliths had constant hydrogenation rates. Again in this example, Catalyst A which had half the metal loading to that of Catalyst B gave an equal hydrogenation rate.

EXAMPLE 3

Evaluation of Monolith Catalysts Without a Cosolvent-Two-Phase Hydrogenation

The procedure of Example 2 was repeated with the exception of the monolith catalyst and the immiscible feed consisted initially of 34 wt. % nitrobenzene, 48 wt. % aniline and 18 wt. % water. The reaction temperature and pressure were 140° C. and 400 psig respectively.

The hydrogenation rates for Example 3 are shown in Table 3.

TABLE 3

Pd on Carbon Monolith Hydrogenation Catalyst in Two Immiscible Phases

| Catalyst | Layer | Rate[1] (initial) | Sel to Aniline |
|---|---|---|---|
| A | polymer network/carbon | 124 | 97 |
| D | carbon composite | 19 | 97 |
| E | carbon composite | 21 | 78 |
| G | cordierite/no carbon | 17 | 96 |

[1]moles $H_2$ per $m^3$ catalyst per second; 140° C.; 400 psig; 1500 rpm

The polymer network/carbon coated cordierite, Catalyst A, and the carbon composite Catalysts D and E all gave nearly constant hydrogenation rates in two immiscible phases when the hydrogen uptake curve was re-plotted as the hydrogenation rate vs. time. There was a marked drop in aniline selectivity with Catalyst E which had a very high surface area. Note the high reaction rate for Catalyst A even though there was a significant amount of water in the reaction product.

COMPARATIVE EXAMPLE 4

Evaluation of Monolith Catalysts For Nitrobenzene Hydrogenation Using a Cosolvent, Isopropanol The procedure of Example 1 was repeated with the exception of the monolith catalyst employed in the hydrogenation. Catalyst J was made from cordierite and the carbon layer was made by a modified carbonization procedure. The carbonization procedure consisted of 650° C. with a $N_2$ purge for 2 hours followed by 5% $O_2/N_2$ at 450° C. for 40 minutes. The surface area by $N_2$ BET is 40–70 $m^2$ per gram.

Table 4 illustrates the effect of a high temperature carbonization procedure on the hydrogenation activity. Hydrogenation was carried out at a concentration of 40 wt. % NB in isopropanol. As the surface area of the monolith increases the hydrogenation activity decreases.

TABLE 4

Pd on Carbon Monolith Hydrogenation Catalyst in One Liquid Phase

| Catalyst | Layer | Rate (initial)[1] | Rate (final) | Sel. to Aniline[2] | $N_2$ BET ($m^2$/gram) |
|---|---|---|---|---|---|
| A | polymer network/carbon | 92 | 91[3] | 97 | <1 |
| B | polymer network/carbon | 61 | 74[3] | 98 | 12 |
| J | carbon | 37 | 24[4] | 99 | 40–70 |

[1]Moles $H_2$ per $m^3$ catalyst per second
[2]Selectivity determined at final experiment
[3]Final rate is the eighth experiment at the same set of conditions
[4]Final rate is the seventh experiment at the same set of conditions The results show that the high temperature carbonization of the network polymer for Catalyst B using furfuryl as was used in forming Catalyst A resulted in producing a higher surface area catalyst and significantly lower hydrogenation rates.

EXAMPLE 5

Evaluation of Monolith Catalysts for Nitrobenzene Hydrogenation

The procedure in Example 1 was repeated and a comparison was made between one liquid phase and two liquid immiscible phases. The molar concentration of nitrobenzene in the one liquid phase and two liquid immiscible phase experiments was the same. Table 5 shows the rate of hydrogenation at 50% conversion for three catalysts with different carbon surface areas.

TABLE 5

Pd on Carbon Monolith Hydrogen Catalyst

| Catalyst | Layer | Liquid Phases | Rate[1] | Sel. To Aniline | $N_2$ BET $m^2$/gram |
|---|---|---|---|---|---|
| A | polymer network/carbon | 1[2] | 91[4] | 97 | <1 |
|   |   | 2[3] | 46[4] | 99 |   |
| F | polymer network/carbon | 1[2] | 46[4] | 99 | <1 |
|   |   | 2[3] | 41[4] | 99 |   |
| J | polymer network/carbon | 1[2] | 24[5] | 99 | 40–70 |
|   |   | 2[3] | 21[5] | 99 |   |

[1]moles $H_2$ per $m^3$ catalyst per second; Pd/C/cordierite
[2]One phase: 2.97M NB (40 wt %) in isopropanol
[3]Two phases: 2.97M NB (34 wt %) in 48 wt % aniline and 18 wt % water
[4]120° C.; 200 psig; 1500 rpm
[5]140° C.; 200 psig; 1500 rpm The Catalysts, A and F, in general, have faster hydrogenation rates in either one phase or two phases when the total surface area is less than 40 $m^2$/gram. Catalyst A showed a difference in reaction rate depending on whether the reaction medium was one phase or two phases. Surprisingly, on the other hand Catalyst F or Catalyst J had equal to or only slightly improved hydrogenation rates when going from two liquid phases to one liquid phase.

What is claimed is:

1. In a process for the heterogeneous catalytic hydrogenation of an organic compound in the presence of water to produce a hydrogenated reaction product, the improvement which comprises:

effecting the hydrogenation of an immiscible two phase mixture of said organic compound, said hydrogenated reaction product and said water in the absence of a cosolvent therefor, and, utilizing a monolith catalytic reactor comprised of a catalytic metal and a monolith support having from 100 to 800 cpi for the heterogeneous catalytic hydrogenation.

2. The process of claim 1 wherein the immiscible mixture is passed through said monolith catalytic reactor at a superficial velocity of from 0.1 to 2 meters per second.

3. The process of claim 2 wherein the organic compound and hydrogenated product has a solubility of less than 8 g/100 g water at 25° C.

4. The process of claim 3 wherein the organic compound used in the hydrogenation reaction is selected from the group consisting of nitro-organics, acid anhydrides and the reaction products of a ketone or aldehyde with ammonia or a primary or secondary amine.

5. The process of claim 4 wherein the monolith support has a polymer network/carbon carbon coating applied to its wall surface and the catalytic metal is applied to the surface of the polymer network/carbon coating.

6. The process of claim 5 wherein the organic compound is a nitroaromatic compound.

7. The process of claim 6 wherein the nitroaromatic compound is nitrobenzene, nitrotoluenes, nitroxylenes, nitroanisoles and halogenated nitroaromatics where the halogen is Cl, Br, I, or F.

8. The process of claim 7 wherein the polymer network/carbon coating is formed from a furfuryl alcohol polymer.

9. The process of claim 8 wherein the total surface area of the monolith catalyst as measured by the $N_2$ BET method is from 0.1 to 15 $m^2$/gram.

10. The process of claim 9 wherein the carbonization temperature of the polymer network/carbon coating is from 250 to 350° C. and the length of carbonization procedure is from to 0.1 to 3 hrs.

11. The process of claim 2 wherein the cpi in the monolith catalytic reactor is from 200 to 600.

12. The process of claim 11 wherein the catalytic metal deposited on the surface of the is Group VIb, Group VIIb, or Group VIII or Group Ib metal.

13. The process of claim 12 wherein the catalytic metal is selected from the group consisting of ruthenium, palladium and platinum.

14. The process of claim 2 wherein the residence time of the immiscible mixture in the monolith reactor is from 0.5 to 120 seconds.

15. The process of claim 5 wherein the organic compound is selected from the group consisting of maleic anhydride and phthalic anhydride.

16. The process of claim 5 wherein the organic compound is the reaction product of a ketone or aldehyde with ammonia or a primary or secondary amine and the ketone or aldehyde is selected from the group consisting of cyclohexanone, methyl isopropyl ketone, and formaldehyde.

* * * * *

UNITED STATES PATENT AND TRADEMARK OFFICE
CERTIFICATE OF CORRECTION

PATENT NO.   : 6,479,704 B1
DATED        : November 12, 2002
INVENTOR(S)  : Andrew Francis Nordquist et al.

It is certified that error appears in the above-identified patent and that said Letters Patent is hereby corrected as shown below:

Column 12,
Line 16, after the words "surface of the" insert the word -- monolith --.
Line 16, after the word "is" insert the word -- a --.

Signed and Sealed this

Thirtieth Day of December, 2003

JAMES E. ROGAN
*Director of the United States Patent and Trademark Office*